United States Patent [19]

Mathies

[11] Plant 4,944

[45] Nov. 16, 1982

[54] MAPLE CALLED DEBORAH

[75] Inventor: John Mathies, Chilliwack, Canada

[73] Assignee: John Holmlund Nursery Co., Gresham, Oreg.

[21] Appl. No.: 188,012

[22] Filed: Sep. 17, 1980

[51] Int. Cl.[3] ..... A01H 5/00
[52] U.S. Cl. ..... Plt./51
[58] Field of Search ..... Plt./51

[56] References Cited

U.S. PATENT DOCUMENTS 1,748 9/1958 Flemer ..... Plt./51

OTHER PUBLICATIONS

Wyman, D. *Trees for American Gardens,* pp. 121 and 122, The MacMillan Company, N. Y. 1951.

Viertel, A. T., *Trees, Shrubs and Vines,* Depictions 501–516, State University College of Forestry at Syracuse, 1959.

*Primary Examiner*—James R. Feyrer
*Attorney, Agent, or Firm*—W. A. Snow

[57] ABSTRACT

This disclosure concerns a new and distinct variety of a new cultivar of *Acer platanoides* characterized by its rapid, vigorous, straight growth, and much taller than normal for the species during the first year's growth, dense branching habit and large leaves.

4 Drawing Figures

BACKGROUND OF THE INVENTION

This new variety of maple tree was discovered by me in a bed of Schwedler Norway maple trees in Vancouver, British Columbia, on cultivated property. During the past several years, I have asexually reproduced this maple tree, by budding, at Cannor Nursery, Chilliwack, British Columbia, and at John Holmlund Nursery, Gresham, Oreg. At the present time, there are several thousand of this variety growing true to form and they are rapid, erect growers.

DETAILED DESCRIPTION OF THE DRAWINGS

Figure 1:
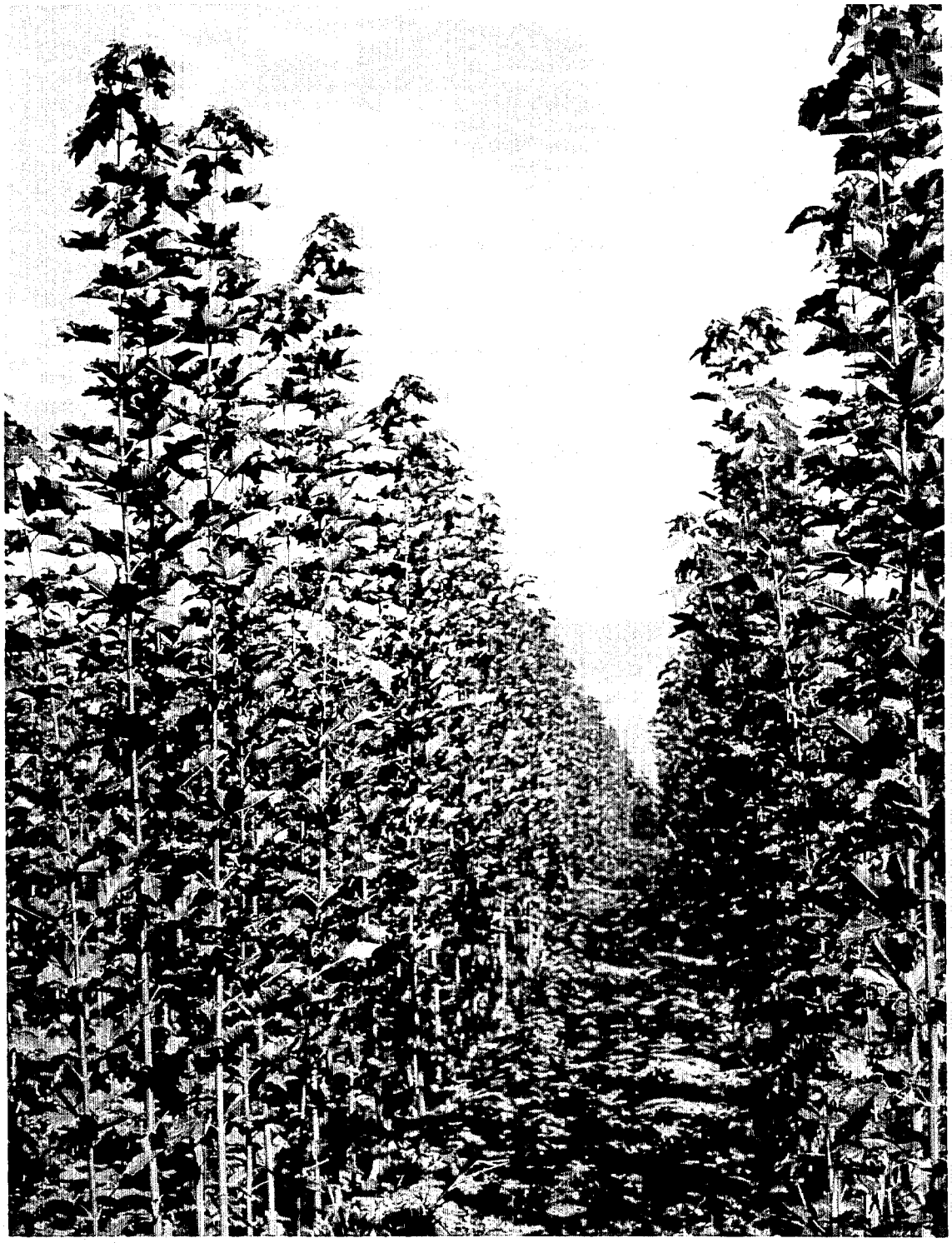
FIG. 1 is a photograph of rows of stock plants at the age of one year at the John Holmlund Nursery.
Figure 2:
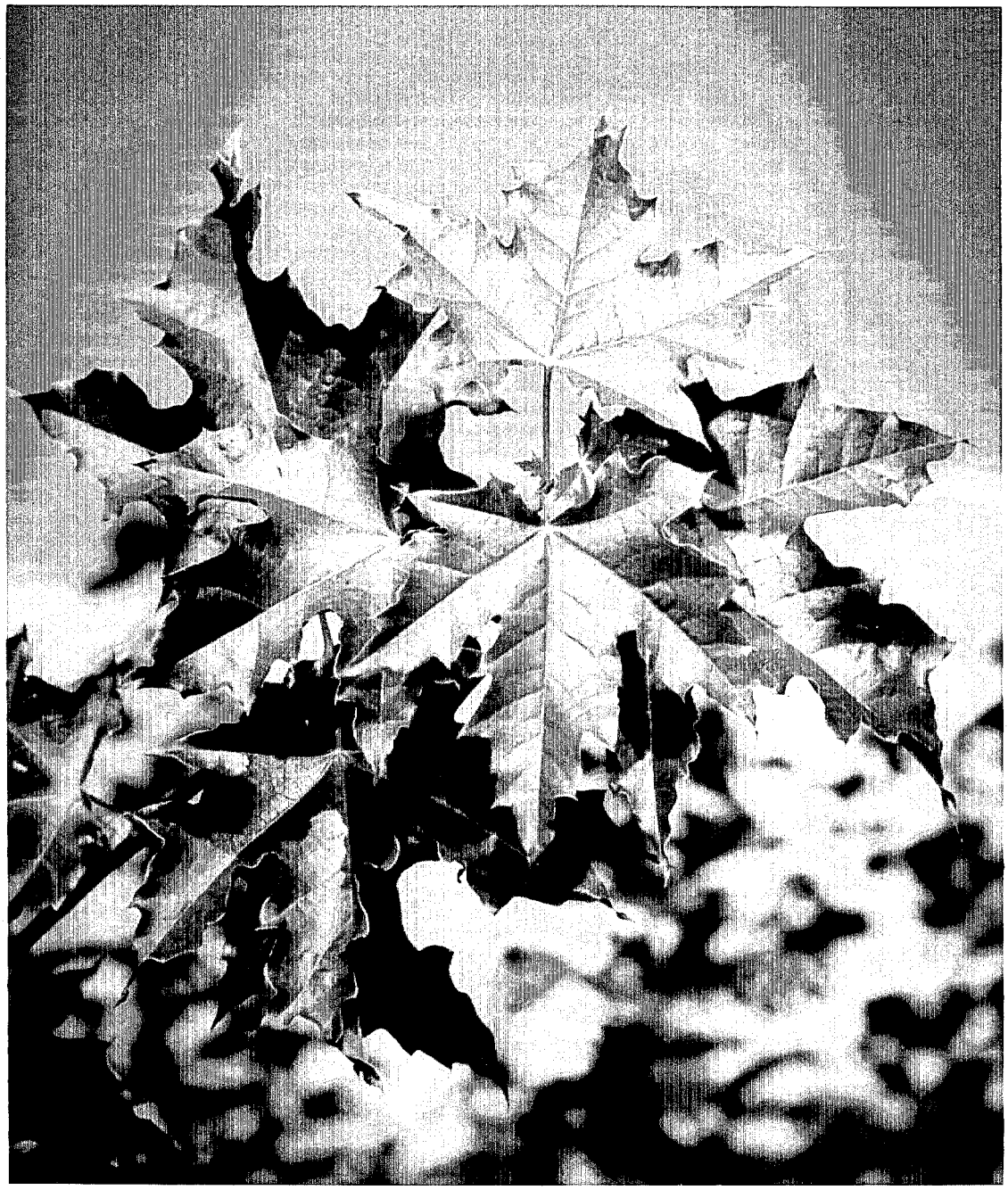
FIG. 2 is a photograph which shows the leaves in their initial red coloration, and in various stages, turning to their mature green color.
Figure 3:
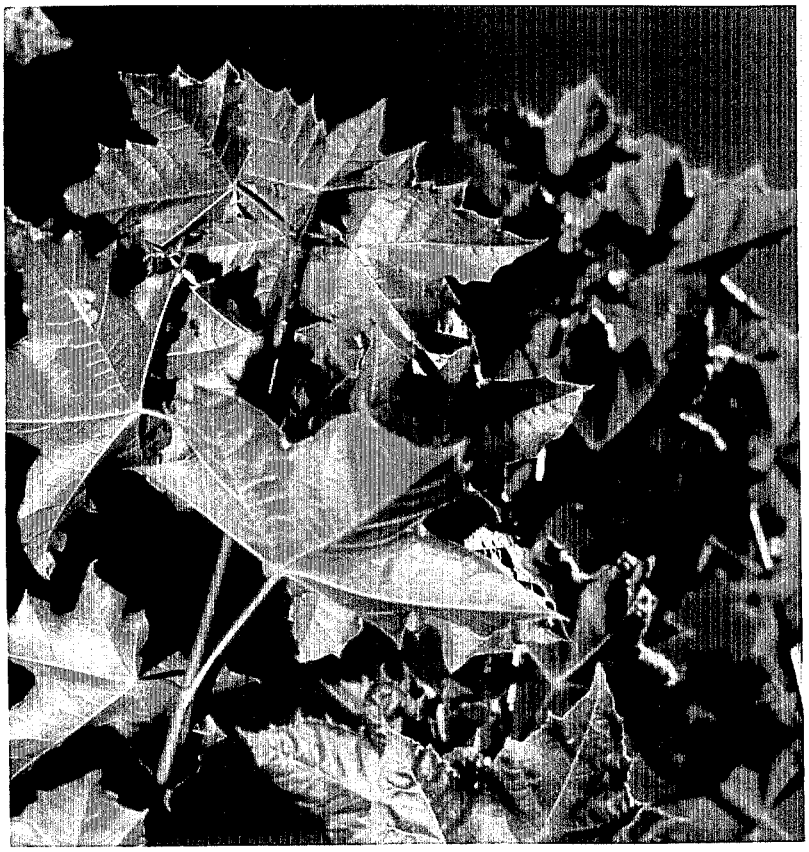
FIG. 3 is a close-up photographic view of the leaves.
Figure 4:
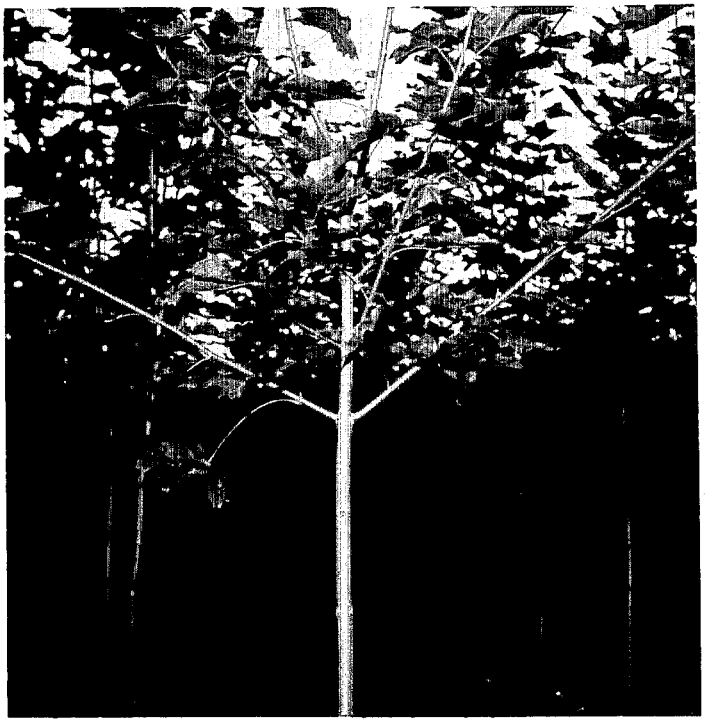
FIG. 4 is a photograph which shows the branching of the stems.

The following is a description of my new maple tree with color designations according to The R.H.S. Colour Chart published by The Royal Horticultural Society of London, England, the stated observations having been made of trees growing at Gresham, Oreg.:

Origin: Seedling.
Parentage: *Acer platanoides.*
Classification:
*Botanic.*—*Acer platanoides.*
*Commercial.*—Norway Maple.
Height:
*At maturity.*—50 to 60 feet.
Trunk size: Sturdy; smooth, grey-brown up to 3 to 4 inches in diameter; becomes ridged and furrowed after a time and the bark color becomes greyish-black.
Growth rate: Varies with climate.

*Present experience.*—10 to 12 feet from bud to end of one year. After first year, everything above 6 feet removed. Second year growth rate up to 12 to 14 feet. Growth very vigorous and erect for species. Oval rounded crown, cold hardy to minus 35° F. in Zone 3 at Arnold Arboretum; can be grown south to Zone 8.

Crown: Uniformly oval-rounded because of numerous branches that arise from trunk; not as wide spreading as typical Norway maple; very dense canopy because of even distribution of foliage throughout the branches.

Branches: Form strong crotches that are resistant to ice and wind damage.
*Angle of attachment.*—About 70 degrees.
*Spacing.*—From 6 to 10 inches.
*Bark.*—Similar to Norway Maple.

Leaves: Opposite, 4 to 7" across, 4 to 6" high, 5-lobed, lobes acuminate, remotely dentate with 5 to 10 pointed teeth, margins prominently crinkled and undulating especially on new growth but maintaining the characteristics on mature leaves, glabrous above, bearded in axils of veins; petiole 3 to 6" long, deep maroon, glabrous, with milky juice.

Color:
*Ruby-red on new growth.*—RHS 819.
*Deep maroon on newly matured leaves.*—RHS 1030/3.
*Dark green on older leaves.*—RHS 1060/3 Color changes occur as leaves mature; time of each color change is dependent on climatic conditions; the cooler the weather the longer the red or maroon stages persist; average time from the ruby-red to the dark green stage is 4 to 6 weeks. Fall color usually not significant but under excellent conditions will develop a golden yellow.

Flowers: Each ⅓" diameter flower is borne in a terminal 15 to 18 flowered, 1½ to 2½" diameter corymb, flowers greenish yellow tinged with reddish purple; flowers appear before the leaves in late April to early May in Gresham, Oreg., and are effective for 12 to 18 days.

Fruit: Samara, borne in pendulous corymbs; each corymb with 10 to 15 pairs of samaras; each 1 to $1\frac{1}{2}''$ long with a prominent membraneous, light brown wing and brownish nutlet at maturity; mature in Gresham, Oreg., between October 10 and October 30, not ornamental and usually hidden by the foliage.

Insect and disease resistance: Excellent; displays good resistance to leaf hoppers and verticillium wilt, two common problems of Norway maple; the thick leathery, dark green leaves are more resistant to leaf scorch than Norway maple; this may be in part due to the thicker cuticle (waxy deposits on the leaf surface).

This new variety most resembles Schwedleri but Schwedleri has an undulating trunk whereas my new variety is very erect and grows twice as high as Schwedleri. Also, the young leaves are a much deeper red than Schwedleri.

As seen in the drawings, my new variety grows very tall and erect and has leaves which are red and turn green with age, and the leaves appear to be more dense in number for the species. The portions of the tree above six feet are cut off after the first year and during the second year it grows even higher, from twelve to fourteen feet.

The outstanding characteristics of my new variety which distinguish it from other purple or red leaf varieties of Norway and all other maples include:

(1) New growth of a rich ruby-red that changes to deep maroon and finally dark green as the leaves mature.

(2) Young leaves wrinkled with distinct deeply impressed veins and pronounced crinkled and undulating margin.

(3) Petioles, like leaves, emerge ruby-red but instead of fading to dark green change to a deep maroon; a color that is maintained throughout the time the leaves are present.

(4) Mature leaves are a leathery dark green and show good resistance to leaf scorch which occurs on leaves of the typical Norway maple.

(5) A tall oval-rounded crown which is more upright than is typical of most Norway maples which have a rounded or broad-rounded crown.

(6) A straight, sturdy trunk, even in youth, that supports the secondary branches and results in a tree that requires minimal staking.

(7) A very dense, uniform canopy develops owing to the numerous branches that develop from the main trunk.

(8) A rapid rate of growth that allows production of 10 to 12′ high trees in one year from budded stock. In the second year caliper increase to $1\frac{1}{2}$ to $1\frac{3}{4}''$ can be expected with a good crown and height of 12 to 15′.

I claim:

1. A new and unique variety of Norway maple tree, as herein described and shown, characterized by a vigorous, oval-rounded growth habit; strong, sturdy trunk; excellent insect and disease resistance; and unique leaf development; the new leaves are a rich ruby-red and display a unique wrinkled-crinkled appearance. The margins are crinkled and undulating, giving the entire tree a bright almost sparkling appearance; as the leaves mature, the ruby-red color changes to deep maroon and finally dark green; the entire color metamorphosis takes place over a 4 to 6 week period; the emerging and newly developing leaves make the tree appear as if it is in flower, gradually this strong focal point is softened as the leaves mature.

* * * * *